US009125967B2

(12) United States Patent
Denry et al.

(10) Patent No.: US 9,125,967 B2
(45) Date of Patent: Sep. 8, 2015

(54) FLUORAPATITE GLASS-CERAMICS

(71) Applicant: University of Iowa Research Foundation, Iowa City, IA (US)

(72) Inventors: Isabelle Denry, Iowa City, IA (US); Julie Holloway, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/075,754

(22) Filed: Nov. 8, 2013

(65) Prior Publication Data

US 2014/0271565 A1    Sep. 18, 2014

Related U.S. Application Data

(60) Provisional application No. 61/725,536, filed on Nov. 13, 2012.

(51) Int. Cl.
  *C03C 10/16*   (2006.01)
  *A61L 27/10*   (2006.01)
  *A61L 27/38*   (2006.01)
  *A61L 24/00*   (2006.01)
  *A61L 24/02*   (2006.01)

(52) U.S. Cl.
  CPC ........... *A61L 27/105* (2013.01); *A61L 24/0005* (2013.01); *A61L 24/02* (2013.01); *A61L 27/3834* (2013.01)

(58) Field of Classification Search
  CPC ....... C03C 10/16; C03C 10/0045; A61K 6/06
  USPC .............................................. 501/3
  See application file for complete search history.

(56) References Cited

U.S. PATENT DOCUMENTS

| | | | | |
|---|---|---|---|---|
| 4,560,666 A * | 12/1985 | Yoshida et al. | ................ | 501/5 |
| 6,620,747 B2 * | 9/2003 | Schweiger et al. | ............ | 501/10 |
| 6,626,950 B2 * | 9/2003 | Brown et al. | ............. | 623/23.72 |
| 2002/0022563 A1 * | 2/2002 | Schweiger et al. | ............... | 501/3 |

* cited by examiner

*Primary Examiner* — Noah Wiese
(74) *Attorney, Agent, or Firm* — Schwegman Lundberg & Woessner, P.A.

(57) ABSTRACT

The present invention provides a highly-sintered fluorapatite glass-ceramic comprising a high Ca/Al or Sr/Al mole-ratio, that possesses a microstructure that induces apatite/bone deposition.

25 Claims, 12 Drawing Sheets

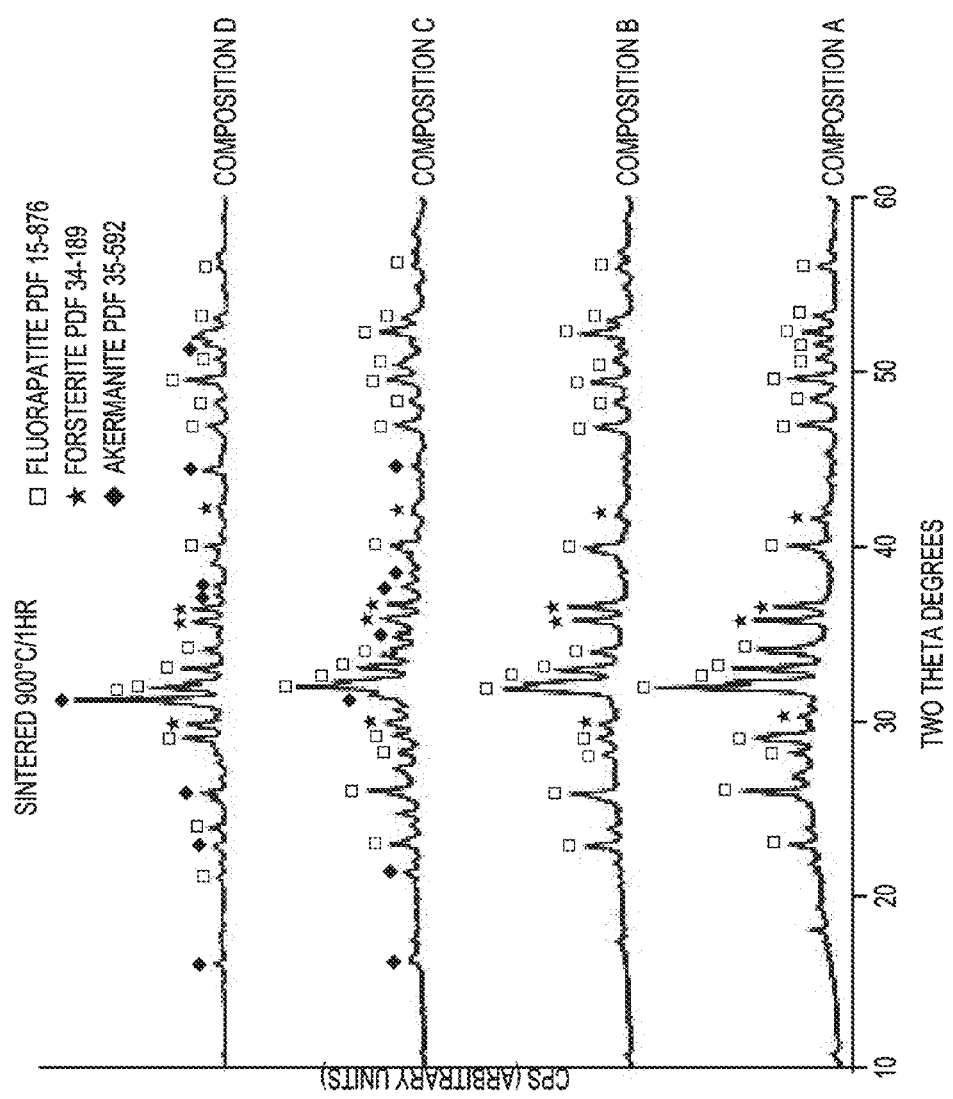

FLUORAPATITE GLASS-CERAMICS

CROSS-REFERENCE TO RELATED APPLICATIONS

This application claims priority from U.S. provisional application Ser. No. 61/725,536 filed Nov. 13, 2012, which is incorporated by reference herein.

GOVERNMENT GRANT SUPPORT

The invention was made with U.S. Government support under R01-DE19972 awarded by the National Institutes of Health (NIH-NIDCR). The Government has certain rights in the invention.

BACKGROUND OF THE INVENTION

Apatite-based glass-ceramics have long attracted interest as synthetic materials for bone replacement [1-5]. They are used in bulk form, powders, coatings, and more recently have been investigated as macroporous scaffolds [6]. The excellent biocompatibility of hydroxyapatite and fluorapatite glass-ceramics is classically related to their chemical and crystallographical similarities with the apatite phase present in bone [7]. Compared to bioinert ceramics such as alumina, the main potential advantage of apatite-based glass-ceramics is the formation of a chemical bond at the ceramic-bone interface [8, 9]. High resolution transmission electron microscopy (TEM) studies have clearly demonstrated the formation of de novo apatite crystals by epitaxial growth on the surface of hydroxyapatite-containing ceramics [10]. Moreover, apatite crystallization in apatite-mullite glass-ceramics has been shown to elicit an excellent bone tissue response after implantation in rat femurs, while the corresponding amorphous glass induced an inflammatory response. [11]

These findings raise the important issue of the role of topography and microstructural features in the pace of in vivo integration of apatite-based glass-ceramics and implant materials [12-14]. Meanwhile, previous work has revealed that fluorapatite glass-ceramics doped with small amounts of niobium oxide crystallized into a very fine dual microstructure composed of submicrometer fluorapatite spherical crystals, together with forsterite polygonal crystals [15]. This microstructure is strongly influenced by the conditions of crystallization heat treatment, namely duration, temperature and cooling rate [16]. Further work revealed that the surface topography associated with this type of microstructure led to excellent attachment, proliferation and differentiation of human mesenchymal stem cells [17]. Recent investigations on the crystallization mechanisms of apatite-mullite glass-ceramics also demonstrated that control of crystal morphology to form arrays of apatite nanocrystals is achievable in this system, through modulations of the glass composition and heat treatment regime [18-20].

Inspired by progress in the fabrication of open-celled ceramics, several processing techniques have been developed to prepare macroporous ceramic scaffolds for bone replacement [21]. Amongst these techniques, one of the most common is the impregnation of a open-cell polymer foam with a ceramic slurry that is later dried and sintered while the polymeric template is eliminated [22]. This polymer foam impregnation technique is an attractive method for producing glass-ceramic scaffolds from bioactive compositions, including hydroxyapatite, fluorapatite and β-tricalcium phosphate (β-TCP)-containing glass-ceramics [23]. However, hydroxyapatite and fluorapatite ceramics are traditionally difficult to sinter, even as mixtures of powders [24-26]. Low temperatures result in high porosity and incomplete sintering, while high temperatures in excess of 1000° C. may lead to decomposition, loss of hydroxyls or fluorine and formation of pyrophosphates [27]. Additionally, in glass-ceramic systems, crystallization may occur during sintering and hinder the densification process [28, 29].

Indeed, it is well established that independently of the nature of the crystalline phases forming, chemical compositional changes in the remaining glassy matrix are likely to induce changes in viscosity, which in turn may prevent adequate sintering [30-32]. Concurrently, several studies have shown that adequate sintering is only possible if sintering precedes crystallization [31, 33].

One way to improve sinterability for a given composition is to extend the working range to allow viscous flow sintering prior to crystallization. This can be done by fine-tuning the glass composition and replacing intermediate oxides such as alumina with alkaline-earth modifiers such as calcium oxide [34, 35]. Moreover, studies in multicomponent bioactive silicate glasses revealed that, when introduced as calcium fluoride, and in the presence of phosphorous pentoxide, calcium causes a decrease in the glass transition temperature, together with an increase in the crystallization temperature, thereby efficiently increasing the processing window [36]. Calcium is also a key component in the development of bioactivity in bioactive glasses [37]. Meanwhile, aluminum oxide has been shown to be detrimental to the bioactivity of calcium silicate glasses [38-40].

SUMMARY OF THE INVENTION

The present invention provides a sintered fluorapatite glass-ceramic body comprising a high $CaO:Al_2O_3$ mole-ratio. The solid body of the invention can be prepared by heating a cast or compressed powder prepared from a fluorapatite glass having a high $CaO:Al_2O_3$ mole-ratio. The cast or compressed powder can be sintered at relatively low temperatures of about 650-900° C. during which good mechanical integrity, and both crystalline phase and specific microstructure inductive for apatite deposition are attained in the resulting solid body. These qualities encourage natural bone deposition upon the present glass-ceramic, e.g., following in vivo implantation, or ex vivo, as a scaffold or a bone replacement or graft material.

The present compositions differ from prior art compositions in that they are prepared by mixing oxides and fluorides to prepare a Nb-doped mixture in the $SiO_2$—$Al_2O_3$—$P_2O_5$—$MgO$—$Na_2O$—$K_2O$—$CaO$—$CaF_2$ system, wherein the mole ratio of CaO to $Al_2O_3$ is adjusted to about 2.5-30:1, preferably to about 3-25:1, e.g., to about 15-20:1. Such a mixture can comprise about 28-38 wt-% $SiO_2$, about 12-18 wt-% MgO, about 1-5 wt-% $Nb_2O_5$, about 20-30 wt-% CaO, about 1-3 wt-% $Na_2O$, about 0-8 wt-% $K_2O$, about 0.5-7.5 wt-% $Al_2O_3$, about 4-6 wt-% $CaF_2$ and about 10-14 wt-% $P_2O_5$. $SrO_2$ is not present in these embodiments of the invention.

The mixture is then heated to form a glass. The glass is cast, shaped or, preferably powdered, the powder is compacted into a mold and/or otherwise shaped into a solid form, and the molded/shaped solid form is heated at about 650-1050° C., preferably at about 700-900° C., e.g., at about 750-875° C. for a period of time effective to form a highly sintered, solid fluorapatite glass-ceramic body. The heating time will vary based on the amount of the compact, e.g., compressed and/or cast glass or glass powder that is used, e.g., from about 0.25-5.0 hrs., preferably about 0.5-2.0 hrs.

Thus, the present invention provides fluorapatite/akermanite glass-ceramic compositions that are sinterable at temperatures as low as about 650-750° C., yielding a density of the final product as high as about 99.5% of the theoretical density. For example, the degree of sintering is about 85%-99.1%, including about 90-99%. In addition, the composition of the invention exhibits a unique microstructure composed of micron-sized spherulitic ("flower shaped") fluorapatite crystals that can enhance apatite deposition and growth in vivo, as well as enhance cultured cell differentiation and production of both collagen fibers and calcium phosphate-rich nodules as tested in vitro. The present glass-ceramics exhibit a density of at least about 2.87, e.g., about 2.9 to about 2.96.

There are no significant differences in either particle diameter or crystal number density between the above-described sintered mixture that is caused by varying the heating rate. After heating to 785° C./4 h at 30° C./min. or heating to 750° C./1 h at 2° C./min. The identical microstructure is obtained. This is a significant widening of the thermal processing parameters available, e.g., for scaffold fabrication.

Replacing a predetermined amount of the CaO with strontium oxide (SrO), for example, up to 24 mole-% (0 mole-% CaO) can increase the number of crystallization sites formed during sintering, while decreasing the fluorapatite crystal size. Both the density and the solubility in neutral and acidic buffers increased with increasing SrO content. Such modified Ca/Sr or Sr glass-ceramics can enhance bone formation and osseointegration.

The density of such SrO-containing glass-ceramics can be as high as about 3.3-3.5, e.g., about 2.9-3.4. SrO can be present when CaO is absent. The mole-ratio of SrO:CaO can be about 3-1:1. The mole ratio of SrO:$Al_2O_3$ can be about 2.5-30:1.

The present ceramics can be used as a bulk or macroporous bone graft substitutes or bone replacement materials. These include load bearing and non-load bearing bone replacements, e.g., macroporous scaffolds, as described hereinabove.

As used herein, the term "body" refers to a solid of any useful size or shape, including, without limitation, particulates such as powders, shaped and molded forms and the like.

As used herein the term "about" is defined to encompass art-recognized variations in precision of the measurement or measuring device.

BRIEF DESCRIPTION OF THE FIGURES

FIGS. 1A-1D. X-ray diffraction patterns of the various glass-ceramics after heat treatment for one hour at 775° C. (Panel A); 800° C. (Panels B and D); 900° C. (Panel C). X-ray conditions for scans in FIG. 1D: 40 kV, 44 mA, 0.2 deg/min., Si powder calibration standard (NIST 640d).

DETAILED DESCRIPTION OF THE INVENTION

Figure 1A:
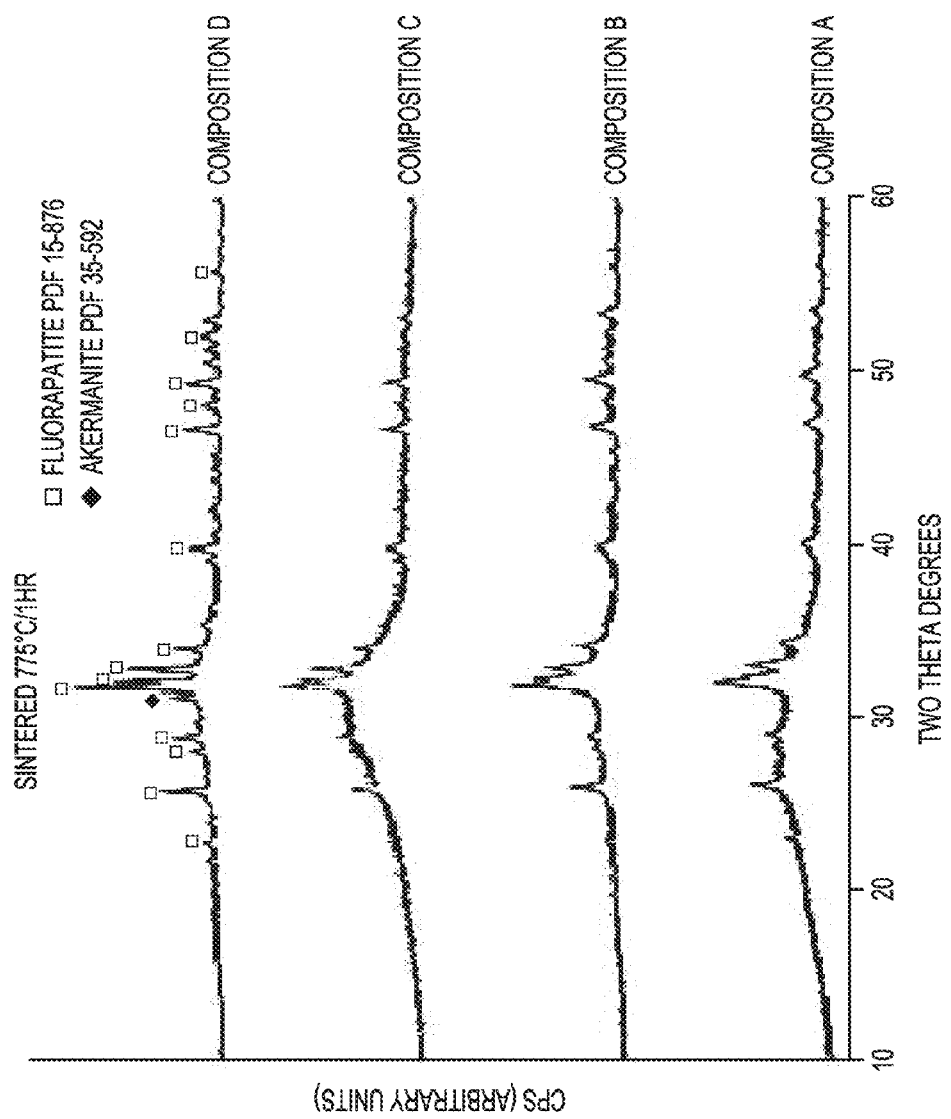

Fluorapatite glass-ceramics have been shown to be excellent candidates as scaffold materials for bone grafts, however, scaffold production by sintering is hindered by concurrent crystallization of the glass. The present invention is based on the effect of Ca/Al ratio on the sintering behavior of Nb-doped fluorapatite-based glasses in the $SiO_2$—$Al_2O_3$—$P_2O_5$—MgO—$Na_2O$—$K_2O$—CaO—$CaF_2$ system. Glass compositions with Ca/Al mole-ratio of 1 (A), 2 (B), 4 (C) and 19 (D) were prepared by twice melting the oxide/fluoride powders at 1525° C. for 3 h. The resulting glasses were either cast as cylindrical ingots or ground into powders. Disc-shaped specimens were prepared by either sectioning from the ingots or powder-compacting in a mold, followed by heat treatment at temperatures ranging between 700 and 1050° C. for 1 h. The density was measured on both sintered specimens and heat treated discs as controls. The degree of sintering was determined from these measurements.

X-ray diffraction (XRD) showed that fluorapatite crystallized in all of the glass-ceramics. A high degree of sintering was achieved at 775° C. for glass-ceramic D (98.99±0.04%), and 900° C. for glass-ceramic C (91.31±0.10). Glass-ceramics A or B were only partially sintered at 1000° C. (63.6±0.8% and 74.1±1.5%, respectively). SEM revealed a unique microstructure of micron-sized spherulitic fluorapatite crystals in glass-ceramics C and D. Increasing the Ca/Al ratio promoted low temperature sintering of fluorapatite glass-ceramics, which are traditionally difficult to sinter.

Increasing the amount of calcium oxide at the expense of aluminum oxide increases sinterability by extending the processing range prior to crystallization of fluorapatite.

Replacing a portion, or all, of the CaO with SrO can also be advantageous.

The invention will be further described by references to the following detailed Examples.

Example 1

(A) Materials and Methods

Specimen Preparation—

Four glass compositions with increasing calcium to aluminum mole ratios were prepared by mixing reagent grade oxides and $CaF_2$ (Table 1). Glass compositions with Ca/Al mole ratios of 1(A), 2(B), 4(C) and 19(D) were prepared.

TABLE 1

Chemical composition of the glasses prepared (mol. %).

| Composition | A | B | C | D |
|---|---|---|---|---|
| $SiO_2$ | 33.9 | 33.1 | 32.3 | 31.5 |
| MgO | 22.9 | 22.3 | 21.8 | 21.2 |
| $Nb_2O_5$ | 0.3 | 0.2 | 0.2 | 0.2 |
| CaO | 8.6 | 13.9 | 19.0 | 23.9 |
| $Na_2O$ | 2.5 | 2.4 | 2.4 | 2.3 |
| $K_2O$ | 4.1 | 4.0 | 3.9 | 3.8 |
| $Al_2O_3$ | 10.4 | 7.1 | 3.9 | 0.9 |

TABLE 1-continued

Chemical composition of the glasses prepared (mol. %).

| Composition | A | B | C | D |
|---|---|---|---|---|
| $CaF_2$ | 12.0 | 11.8 | 11.5 | 11.2 |
| $P_2O_5$ | 5.4 | 5.2 | 5.1 | 5.0 |

Fluoride was introduced as calcium fluoride and was added in excess, as 50% losses by volatilization were anticipated. The compositions A-D were melted at 1525° C. for 3 h in platinum crucibles. After quenching in deionized water, the resulting glass frits were powdered and melted again at 1525° C. for 3 h.

The molten glasses were cast to form cylindrical rods (10 mm in diameter; 60 mm in length). The rods were furnace-cooled from 685° C. to room temperature and sectioned into disks (10 mm in diameter; 1 mm thick) using a low speed diamond saw. Specimens were then heat treated in the temperature range 700-1050° C. for one hour at a heating rate of 2° C. per minute. Glass frits from the same compositions were prepared as described earlier.

Frits were powdered and sieved to a particle size of 45 micrometers or less. Disk-shaped specimens (10 mm in diameter; 1 mm thick) were produced by uniaxial pressure using a polyvinylsiloxane mold. Specimens were sintered in air at temperatures ranging between 700 and 1050° C. for one hour.

Crystallization Behavior—

The crystallization behavior was investigated by differential scanning calorimetry (Q600 DSC/TGA, TA Instruments). Analyses were performed on glass frit particles placed in matched platinum-rhodium crucibles under nitrogen gas flow. Aluminum oxide powder (99.99%) served as a reference standard. First, the optimum nucleation temperature (ONT) was determined for each glass composition. This temperature is defined as the "temperature at which the most number of stable nuclei form per volume element" [18]. ONT was investigated by DSC after one hour nucleation holds at various temperatures, followed by full crystallization, according to the method proposed by Marotta et al. [41]. The ONT was determined as the hold temperature leading to the lowest temperature for the first crystallization exotherm. Further DSC experiments were conducted at heating rates of 10, 20, 30 and 40° C./min. on samples nucleated at the ONT. The activation energy of crystallization ($E_C$) for fluorapatite was calculated from the slope of the classical Kissinger plot, using the Kissinger equation [42]:

$$\frac{E_C}{RT_P} = ln\left(\frac{T_P^2}{v}\right) \quad (1)$$

where $T_P$ is the temperature of the crystallization exotherm and $v$ is the heating rate.

The coefficient of thermal expansion and softening point were determined by dilatometry on glass bars sectioned from the cast ingots (Orton dilatometer, Model 1600D). Crystalline phases were characterized by X-ray diffraction on powdered and bulk specimens. Scans were performed in the two-theta range 10-60°, at a scanning rate of 1° C./min. (Miniflex II diffractometer, Rigaku Americas). Additionally, specimens sintered at 800° C./1 h were analyzed at a scanning rate of 0.2 degrees per minute in the two theta range 3-90 degrees at 40 kV and 44 mA in Bragg-Brentano configuration (SmartLab, Rigaku Americas). Peak positions were determined using PDXL-2 analysis software (Rigaku Corporation) after calibration using silicon powder standard (NIST, 640d).

The microstructure was investigated by scanning electron microscopy under secondary electron imaging (Hitachi S-4800 field emission SEM). Specimens were polished to a 0.5 μm finish using as series of abrasives ending with diamond polishing pastes. They were etched with diluted hydrofluoric acid and gold coated prior to SEM examination. A variable pressure scanning electron microscope (VP-SEM, Model 3400, Hitachi High Technologies America, Inc.), coupled with a back-scattered electron detector, was used to perform semi-quantitative Energy Dispersive Spectroscopic analyses on uncoated specimens. X-rays were detected at an accelerating voltage of 15 kV and a working distance of 10 mm (Bruker AXS Microanalyzer). ZAF matrix correction factors were applied in instrumental software calculations.

Sintering Behavior—

The density of bulk glass-ceramic specimens as well as sintered specimens was measured by Archimedes' method. The degree of sintering was calculated assuming 100% theoretical density for bulk heat treated glass-ceramic specimens. The sintering behavior was also assessed by scanning electron microscopy on both as-sintered and sintered and polished specimens.

Statistical Methods—

Results were analyzed by ANOVA and Tukey's test to detect statistically significant differences. A p-value of less than 0.05 was considered statistically significant.

(B) Results

Crystallization Behavior—

Figure 1B:
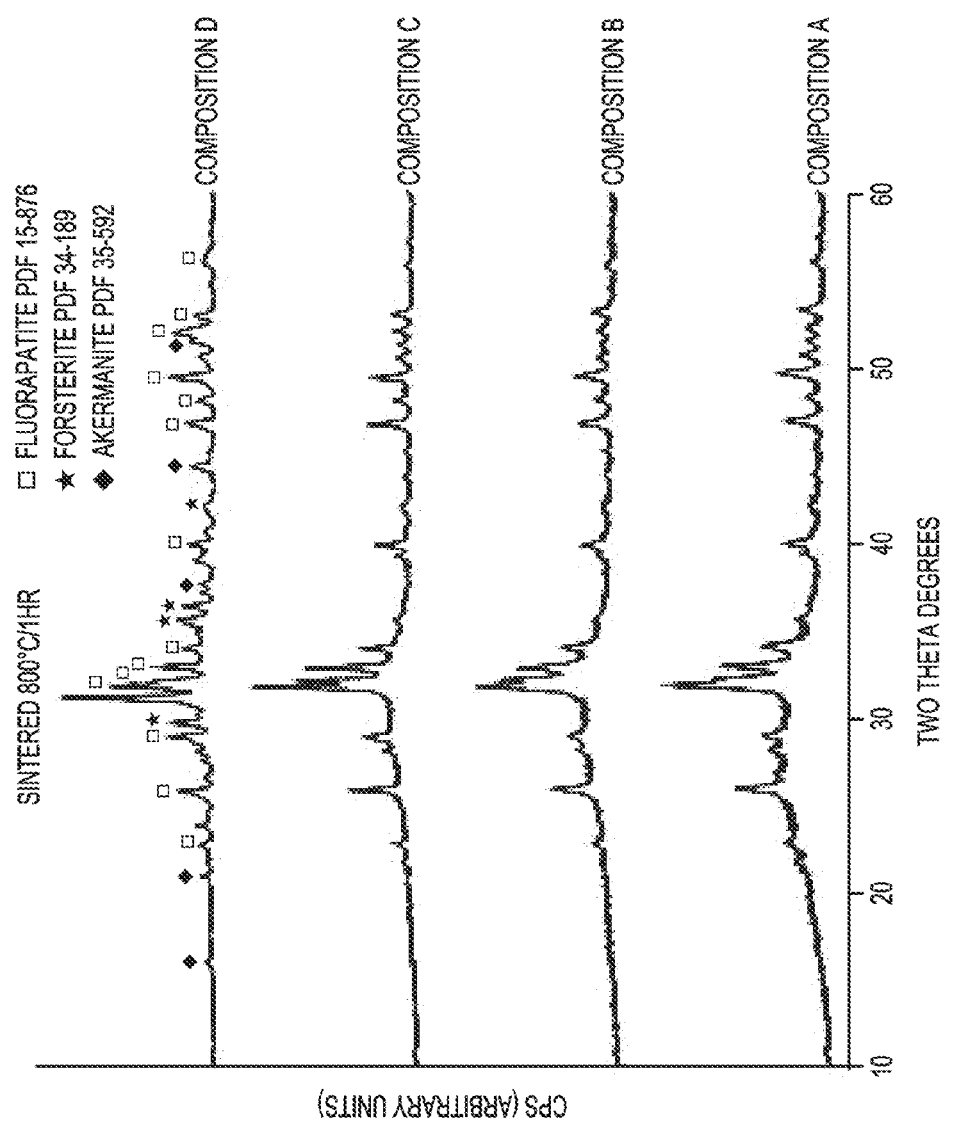
Figure 1D:
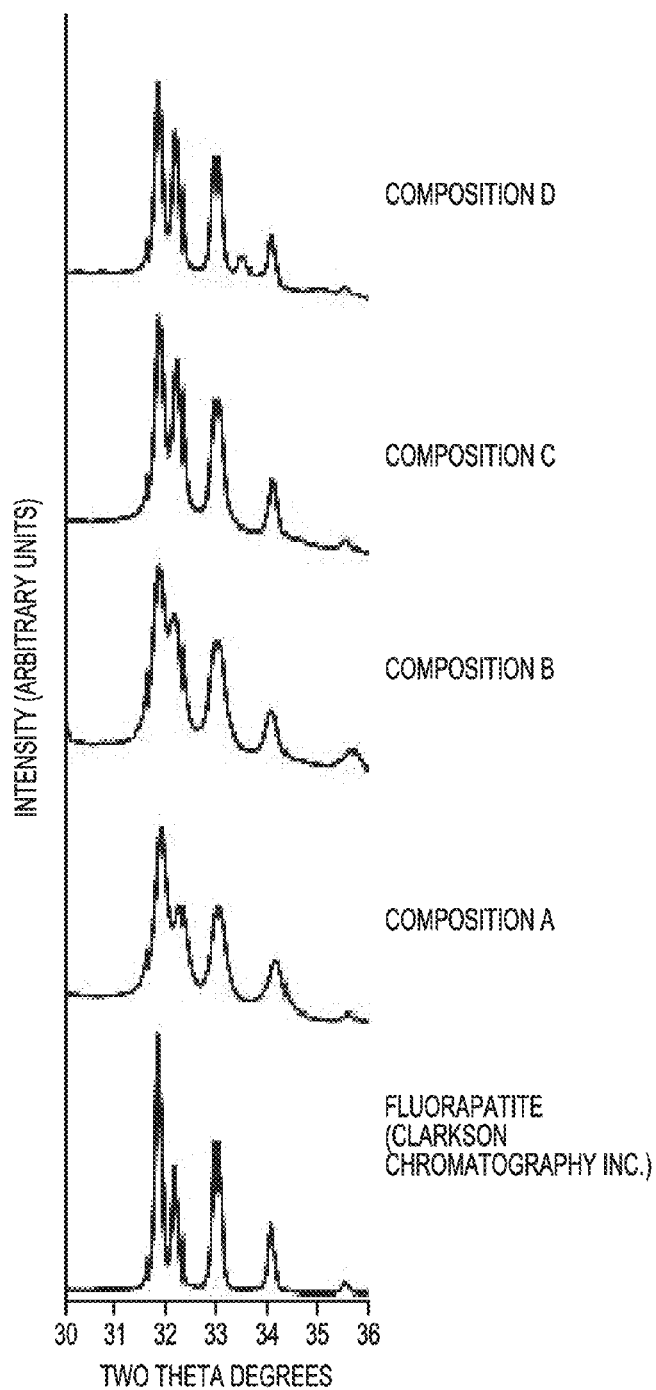

Characteristic X-ray powder diffraction patterns of specimens sintered at 775, 800 or 900° C. for 1 h are displayed in FIG. 1 (A-D). Fluorapatite ($Ca_5(PO_4)_3F$, PDF 15-876) was present for all compositions from 775° C. and up. The figure of merit for fluorapatite was determined using PDXL 2 Data Analysis Software on precision scans performed at 0.2 degree per minute (FIG. 1D) and was less than one for all compositions, indicating an excellent match.

Akermanite ($Ca_2MgSi_2O_7$, PDF 35-592) started to appear at 775° C. for composition D and 900° C. for composition C. It became the predominant phase at 800° C. for composition D. A small amount of forsterite ($Mg_2SiO_4$, PDF 34-189) was found in composition D after heat treatment at 800° C. and in all compositions at 900° C. X-ray powder diffraction patterns obtained on disks sectioned form bulk glass ingots and further heat treated matched those of sintered specimens. Results from differential thermal analyses are summarized in Table 2 and graphically displayed in FIG. 2.

TABLE 2

DSC and dilatometric analyses summary: glass transition ($T_g$), crystallization exotherms ($T_P$), optimum nucleation temperature (ONT), fluorapatite activation energy ($E_a$), coefficient of thermal expansion ($\alpha$) and softening point ($T_s$) for the various glass compositions.

| Glass code | A | B | C | D |
|---|---|---|---|---|
| Ca/Al at. ratio | 1 | 2 | 4 | 19 |
| $T_g$ bulk (° C.) | 659 | 663 | 660 | 638 |
| $T_{P1}$ onset (° C.) | 765 | 809 | 823 | 817 |
| $T_{P1}$ bulk (° C.) | 783 | 833 | 861 | 864 |
| $T_{P2}$ bulk (° C.) | 1062 | 1074 | 1025 | 981 |
| ONT (° C.) | 670 | 700 | 690 | 680 |
| $E_a$ fluorapatite ($kJmol^{-1}$) | 343 | 344 | 348 | 353 |

TABLE 2-continued

DSC and dilatometric analyses summary: glass transition ($T_g$), crystallization exotherms ($T_P$), optimum nucleation temperature (ONT), fluorapatite activation energy ($E_a$), coefficient of thermal expansion ($\alpha$) and softening point ($T_s$) for the various glass compositions.

| Glass code | A | B | C | D |
|---|---|---|---|---|
| Ts (° C.) | 725 | 704 | 693 | 663 |
| $\alpha$ (×10$^{-6}$/° C.) | 9.5 | 10.0 | 11.1 | 11.5 |

For each glass composition, two exothermic peaks were observed. For all compositions, the first exotherm, occurring between 783 and 864° C., is attributed to the crystallization of fluorapatite. According to XRD analyses, the second exotherm, occurring between 981 and 1074° C., is attributed to the crystallization of forsterite in compositions A and B and concurrent crystallization of akermanite and forsterite in compositions C and D.

Figure 2:
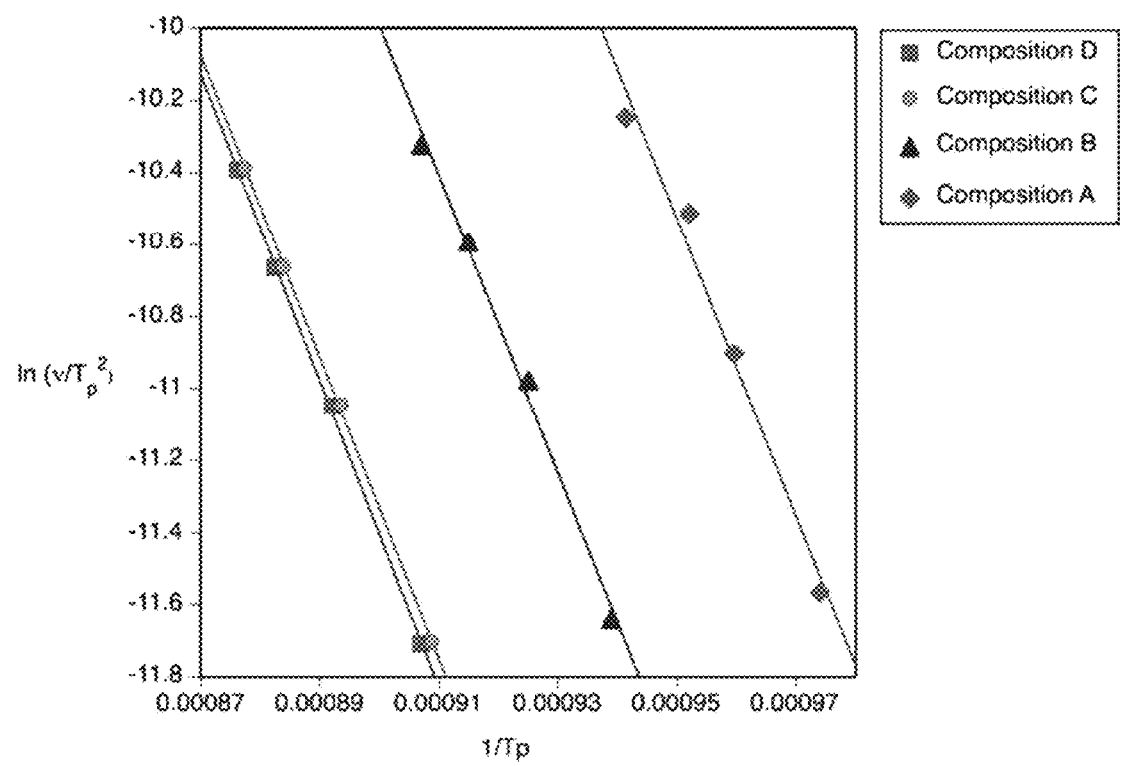
FIG. 2. Kissinger plots of ln $(v/T_p^2)$ as a function of $1/T_p$ for each of the glass compositions.
Figure 3:
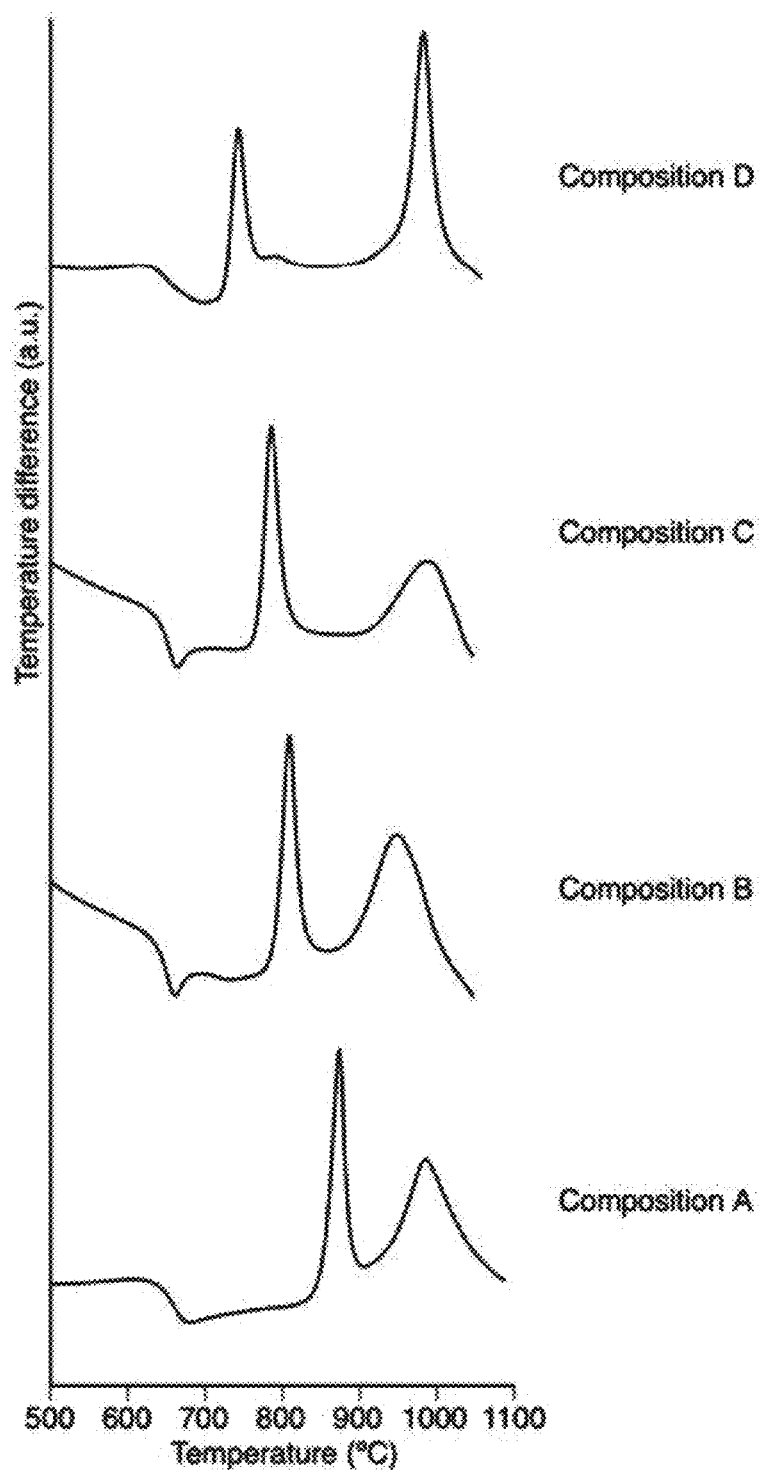
FIG. 3. DSC traces of each glass composition in bulk form (heating rate: 20° $C.min^{-1}$).
Figure 4B:
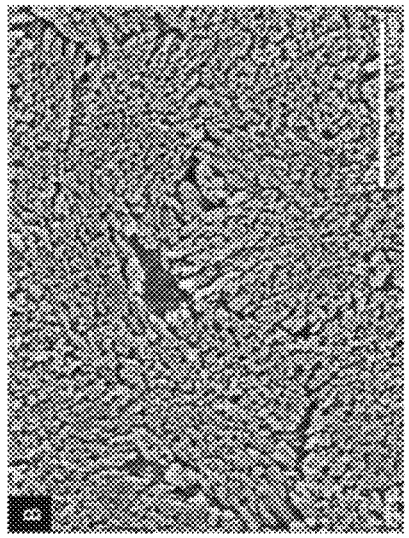
FIGS. 4A-4D. Scanning electron micrographs of the various glass-ceramics after heat treatment at 775° C. for 1 hour. Composition A: (Panel A); Composition B (Panel B); Composition C: (Panel C); Composition D: (Panel D).
Figure 4D:
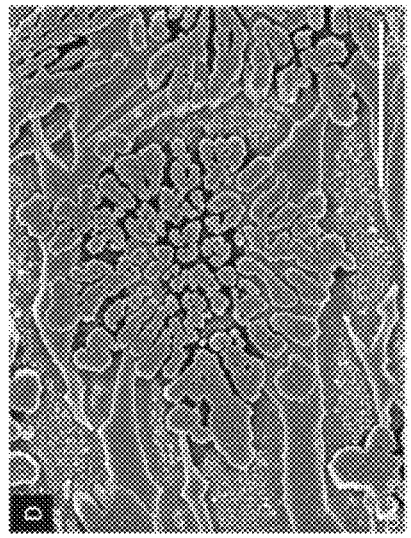
Figure 4A:
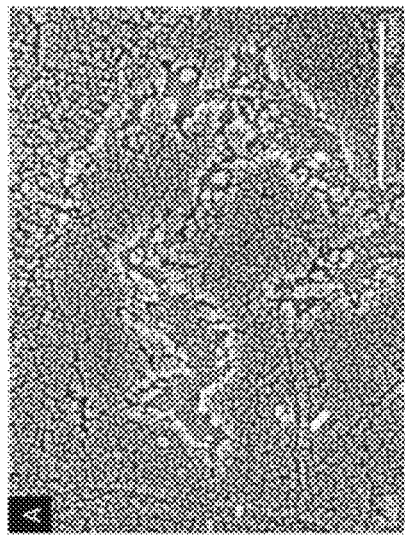
Figure 4C:
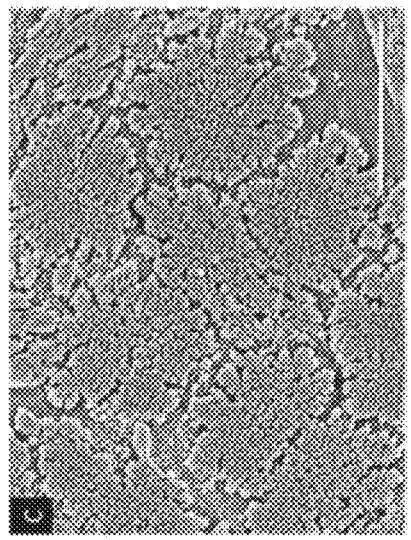
Figure 5A:
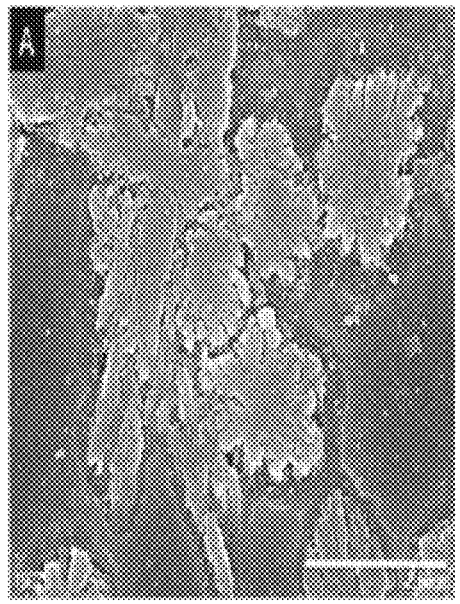
FIGS. 5A-5D. Scanning electron micrographs of glass-ceramic D after heat treatment at 775° C. (Panel A); 800° C. (Panel B); 850° C. (Panel C); 900° C. (Panel D).
Figure 5B:
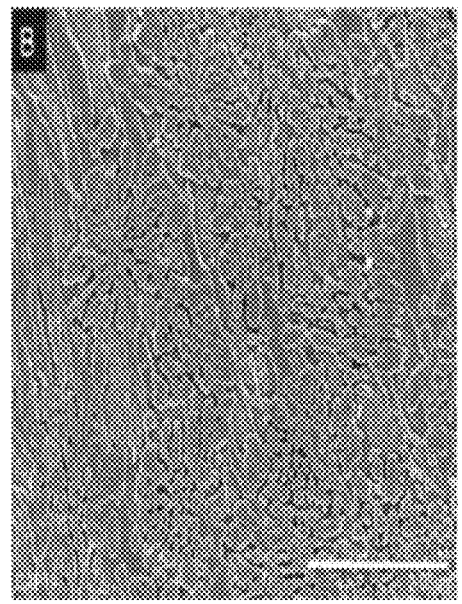
Figure 5C:
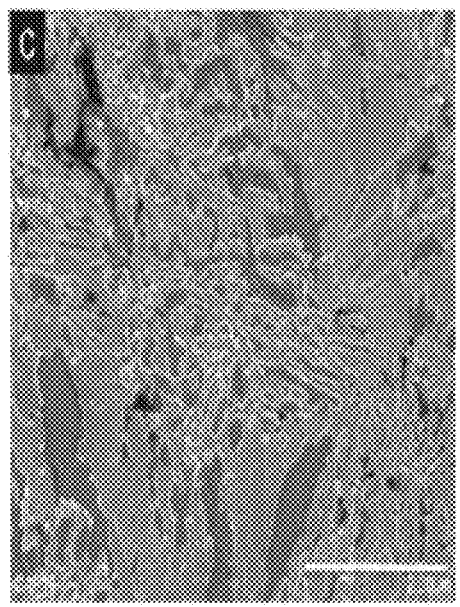
Figure 5D:
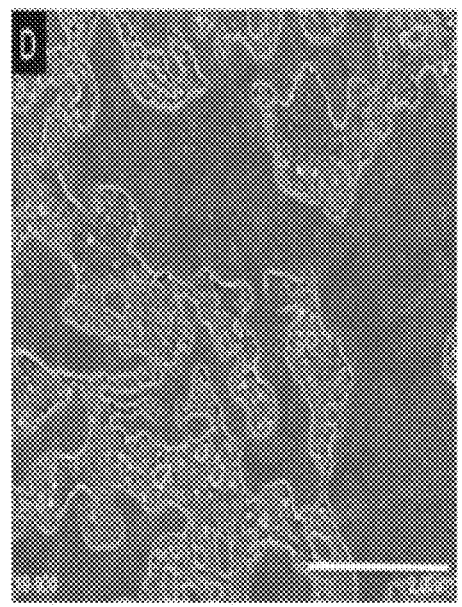

The Optimum Nucleation Temperature varied between 670 and 700° C., depending on the composition. The plots obtained from the Kissinger equation (1), supra, are shown in FIG. 2. The activation energy for the crystallization of fluorapatite slightly increased with increasing the calcium to aluminum ratio and ranged between 343 kJmol$^{-1}$ for composition A to 353 kJmol$^{-1}$ for composition D. The results from dilatometric analyses, including the softening point and coefficient of thermal expansion are listed in Table 2. Increasing the calcium to aluminum ratio led to a decrease of the softening point from 725° C. for composition A to 663° C. for composition D, while the coefficient of thermal expansion increased from 9.5 to 11.5×10$^{-6}$/° C.

The microstructure of the glass-ceramics after heat treatment at 800° C. is shown in FIG. 4, Panels A-D. A fine coast-and-island relict microstructure, characteristic of glass-in-glass phase separation, followed by crystallization of island-shaped fluorapatite crystals can be seen in composition A. Spherulitic fluorapatite crystals are present in compositions B and C, while well developed, flower-shaped fluorapatite crystals are clearly seen in composition D. The evolution of the microstructure with heat treatment temperature for composition D is displayed in FIG. 5 (Panels A-D). Darker island-shaped akermanite crystals started to appear at 800° C., became more defined at 850° C. and dominated the microstructure at 900° C. Results from EDS analyses are summarized in Table 3.

TABLE 3

Chemical composition (at. %) from EDS analyses (SD).

| Element | A | B | C | D |
|---|---|---|---|---|
| O | 60.0 (2.7) | 56.3 (2.7) | 59.3 (3.5) | 52.8 (4.6) |
| F | 3.3 (0.6) | 2.7 (1.3) | 3.5 (0.9) | 3.1 (1.1) |
| Na | 2.9 (0.7) | 2.1 (0.9) | 2.3 (0.3) | 1.8 (0.3) |
| Mg | 7.1 (0.4) | 7.5 (3.1) | 7.2 (0.6) | 7.9 (1.0) |
| Al | 6.2 (0.5) | 4.9 (2.0) | 2.9 (0.3) | 1.1 (0.2) |
| Si | 11.6 (1.0) | 13.1 (5.4) | 12.2 (1.8) | 14.9 (2.4) |
| P | 2.5 (0.2) | 2.8 (1.2) | 2.7 (0.4) | 3.3 (0.5) |
| K | 1.7 (0.3) | 1.5 (0.7) | 1.1 (0.1) | 1.1 (0.1) |
| Ca | 4.4 (0.3) | 8.8 (3.8) | 8.7 (1.4) | 13.6 (2.0) |
| Nb | 0.3 (0.1) | 0.3 (0.1) | 0.3 (0.1) | 0.4 (0.1) |

Sintering Behavior—

Results for density measurements of bulk glasses and glass-ceramics are presented in Table 4.

TABLE 4

Density of glasses and glass-ceramics.

| Composition | Glass | Glass-ceramic |
|---|---|---|
| A | 2.769 ± 0.008 | 2.852 ± 0.008 |
| B | 2.842 ± 0.008 | 2.886 ± 0.008 |
| C | 2.895 ± 0.012 | 2.887 ± 0.014 |
| D | 2.927 ± 0.008 | 2.951 ± 0.005 |

Figure 6:
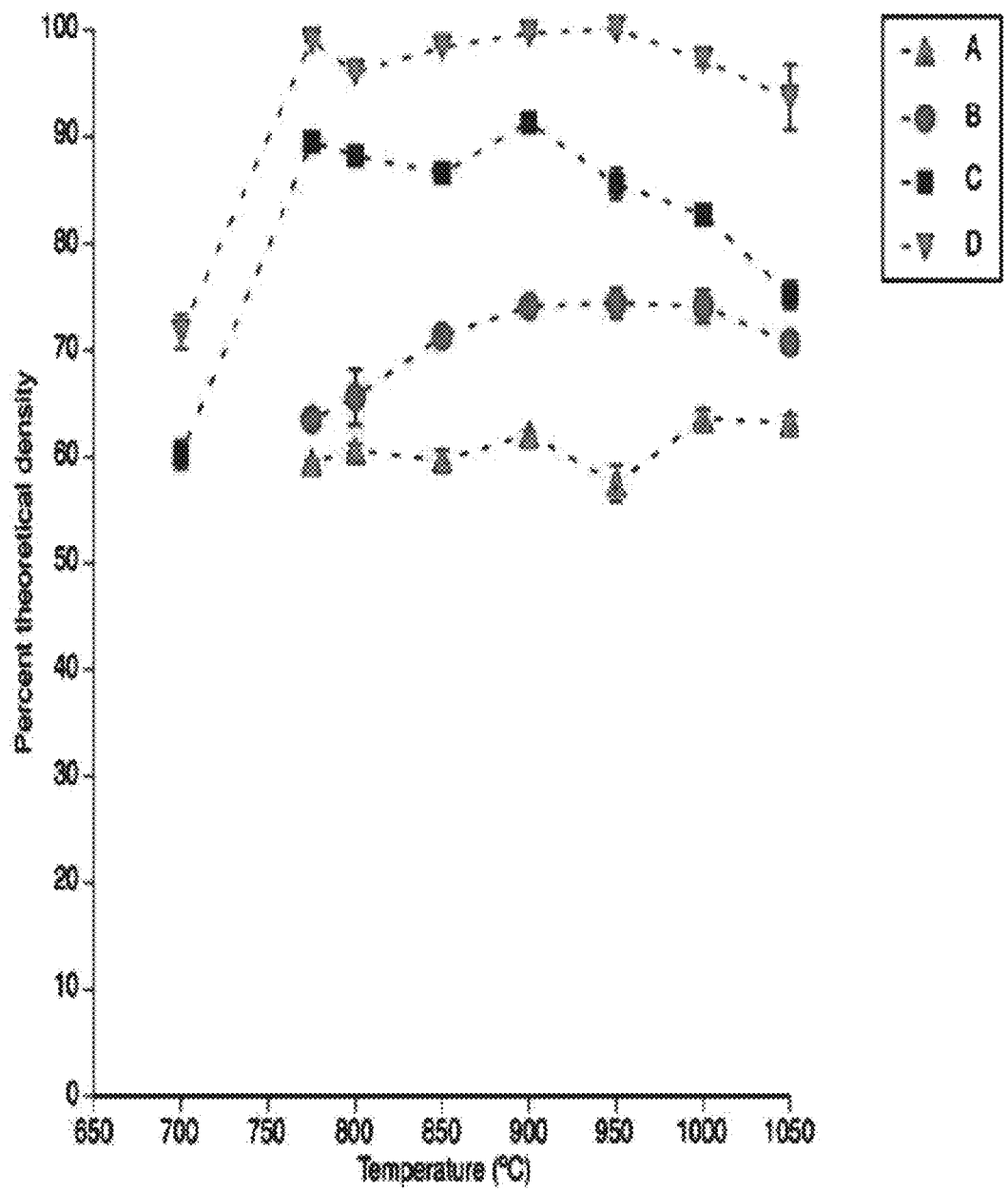
FIG. 6. Degree of sintering as a function of sintering temperature for the various glasses.
Figure 7A:
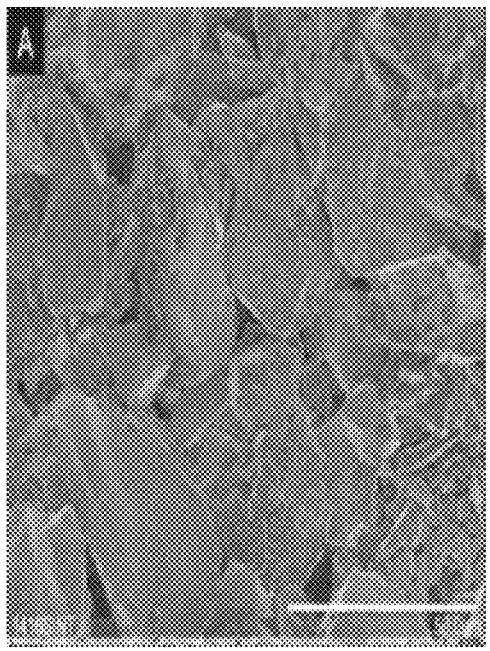
FIGS. 7A-7D. Scanning electron micrographs of the various glass-ceramics after sintering at 775° C. for one hour. Composition A: (Panel A); Composition B (Panel B); Composition C: (Panel C); Composition D: (Panel D).
Figure 7B:
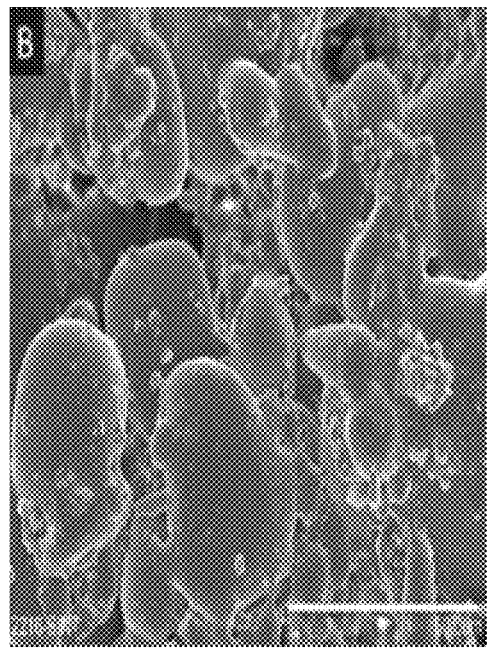
Figure 7C:
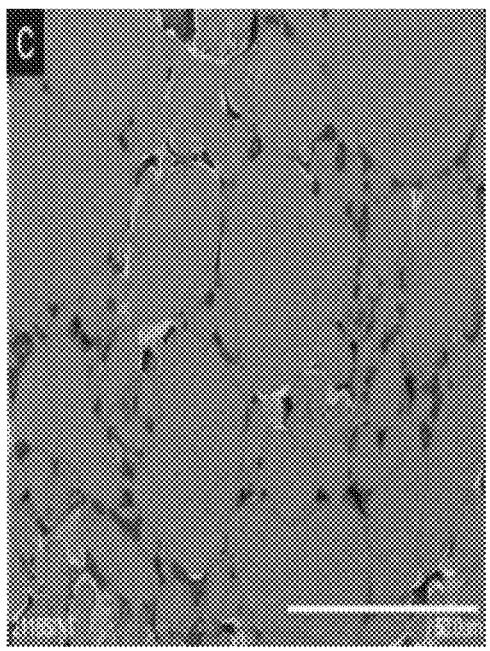
Figure 7D:
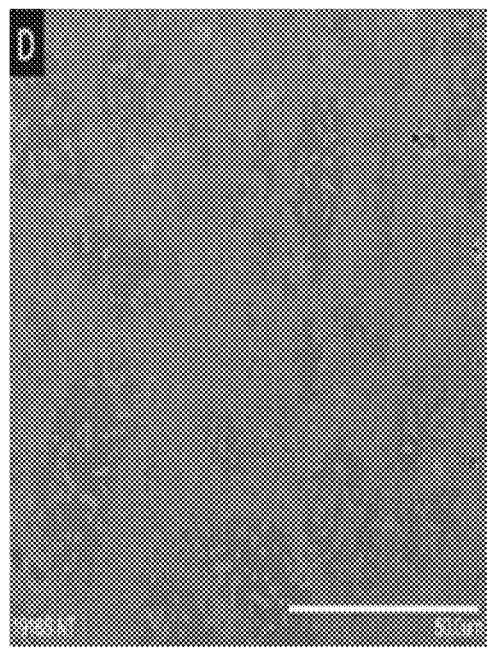

The calculated degree of sintering as a function of temperature is graphically displayed in FIG. 6. The lack of mechanical integrity prevented accurate measurement for compositions A and B after sintering at 700° C. for 1 h. The degree of sintering for composition A only remained around 60%, even after sintering up to 1050° C. for one hour. The degree of sintering for composition B increased slowly from 63.5% at 750° C. up to a maximum of 74.4% at 950° C. for 1 h.

Concurrently, significant changes in the degree of sintering were observed for compositions C and D over the same temperature range. The largest amount of sintering occurred between 700 and 775° C. for both compositions. Composition C reached a maximum of 91% after sintering at 900° C., followed by a linear decrease to 75% as the sintering temperature was raised to 1050° C. The degree of sintering of composition D rapidly reached 99% at 775° C. and remained in this range up to 950° C., while a slight decrease in density was observed to 93.7% at 1050° C. Above 700° C., the overall degree of sintering was significantly different between all compositions ($p<0.0001$). Composition D exhibited the greatest degree of sintering followed by C, B and A. Within groups C and D, sintering at 1050° C. led to a significantly lower degree of sintering than other temperatures ($p<0.0001$).

Figure 8:
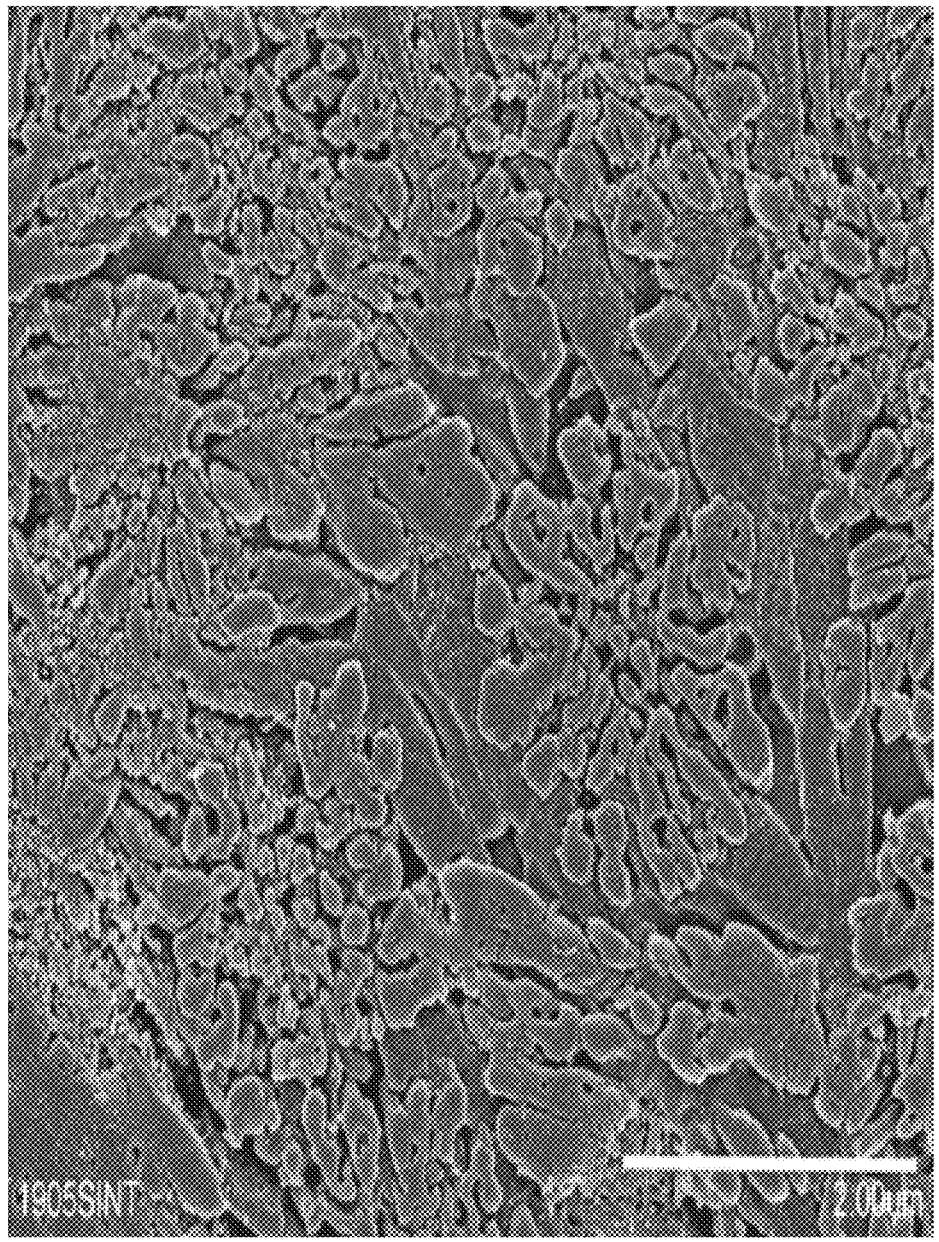
FIG. 8. Scanning electron micrograph of glass-ceramic D after sintering at 800° C. for one hour.
Figure 9:
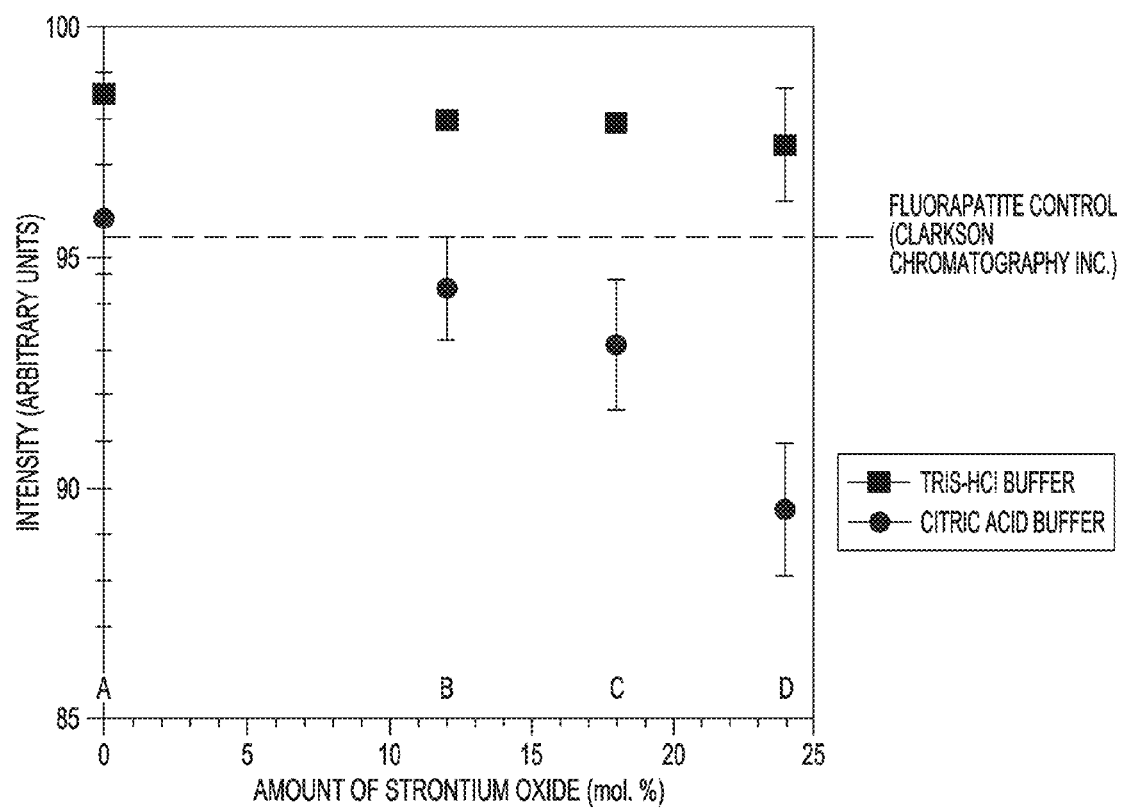
FIG. 9. Chemical solubility as a function of strontium content in TRIS-HCl and citric acid buffer (120 h at 37° C., according to ISO 10993-14).

Scanning electron micrographs of specimens sintered at 775° C. for 1 h are shown in FIG. 7 (Panels A-D). Sharp-angled particles, indicating a lack of sintering, were present for composition A (FIG. 7A). Rounding of the powder particles occurred for composition B, together with some particle necking (FIG. 7B), while interconnected pores remained. A noticeably greater degree of necking, with progressive disappearance of open pores is evident for composition C (FIG. 7C). Only a few pores remain and individual particles are no longer discernable for composition D, indicating that the sintering process is complete (FIG. 7D). The microstructure after sintering at 800° C. for 1 h for composition D is shown in FIG. 8. Flower-shaped fluorapatite crystals similar in shape and size to those observed after heat treatment of bulk specimens at 800° C. for 1 h are present.

(C) Discussion

XRD and DSC results revealed that increasing the calcium to aluminum ratio led to a significant increase from 783 to 864° C. in the crystallization temperature of fluorapatite, accompanied by a slight increase in the activation energy from 343 to 353 kJmol$^{-1}$. Meanwhile, the softening temperature decreased from 725° C. to 663° C. It was previously reported that glasses in the compositional range corresponding to composition A underwent amorphous phase separation, with formation of a droplet phase that later crystallized into small spherical fluorapatite crystals [15, 16]. This particular glass composition has a measured Ca:P ratio of 1.8, with phosphorous being the limiting element to the amount of fluorapatite crystallization. The remaining glassy matrix after FAp crystallization is likely to contain a small amount of fluorine, but very little calcium.

Concurrently, composition D has a measured Ca:P mole ratio of 4.1, phosphorous being again the limiting factor to FAp crystallization, the remaining glassy matrix will contain a substantial amount of calcium. This explains the crystallization of akermanite ($Ca_2MgSi_2O_7$), immediately following that of fluorapatite. The activation energy for fluorapatite crystallization falls within the range of 163 to 682 kJ $mol^{-1}$ reported for other FAp glass-ceramic systems [43]. The slight increase in activation energy for composition D in bulk form was not expected due to the increase in the amount of calcium in the composition. Calcium is a network modifier, expected to lower glass network connectivity and increase viscous flow, thereby inducing a decrease in the activation energy for FAp crystallization.

O'Flynn et al. used a similar experimental design for DSC analyses, with determination of the optimal nucleation temperature and a nucleation hold, to study the crystallization behavior of apatite-mullite glass-ceramics [18]. They first determined the optimal nucleation temperature, and then applied a one hour nucleation hold at that temperature prior to investigating the effect of heating rate on the crystallization exotherms temperature. They observed an increase in the activation energy for fluorapatite crystallization with increasing amounts of calcium fluoride in the glass, with values in the range 292 to 471 $kJmol^{-1}$. It was proposed that higher amounts of fluorine led to a higher nucleation density during the isothermal hold. The creation of these nuclei consuming fluorine could have made crystal growth more difficult, hence increasing the activation energy. The apatite nucleation rate is also likely to increase with increasing the amount of calcium in the glass [44].

It is believed that, in this example, a similar mechanism involving a higher nucleation rate and/or phase separation of a calcium-rich phase, in relation with the subsequent crystallization of akermanite be responsible for a slightly more difficult crystal growth in composition D, ultimately leading to an increase in the activation energy and crystallization temperature of fluorapatite. Although semi-quantitative, EDS analyses confirmed that glass melting was associated with significant fluorine losses by volatilization, they also showed losses in other species such as phosphorous and potassium. However, fluorine losses were anticipated and excess fluorine remained in all compositions with regard to the stoichiometry of fluorapatite, most certainly playing an important role on the behavior of the glasses, by lowering network connectivity and further promoting phase separation [45, 46].

As the glasses phase-separated into Ca—P-rich droplets [16], modifier cations were no longer needed to charge-balance phosphorous in the glass network, allowing a decrease in connectivity. Meanwhile, increasing the amount of charge-balancing calcium available and decreasing the amount of aluminum is likely to have prevented $Al^{3+}$ ions from reaching a four-fold coordination state, also leading to a decrease in connectivity. Therefore, it is believed that both calcium and fluorine led to a decrease in network connectivity, permitting better sintering by viscous flow prior to fluorapatite full crystallization. The observed increase in FAp crystallization temperature, together with a decrease in softening temperature considerably extended the processing window for compositions C and D, which explains the large increase observed in the degree of sintering as a function of calcium to aluminum ratio. This result is also in line with the overall decrease in the glass transition temperature and increase in coefficient of thermal expansion, reported to occur with an increase in $CaO/SiO_2$ ratio in diopside-fluorapatite-wollastonite-based glass-ceramics [31].

Sintering started and nearly reached completion prior to crystallization of fluorapatite in compositions C and D. The poor sintering behavior observed for compositions A and B is likely due to earlier crystallization of fluorapatite, together with lower amounts of calcium in the glassy matrix, as compared to compositions C and D, thereby hindering the sintering process by increasing the viscosity. The crystallization of forsterite ($Mg_2SiO_4$) at higher temperatures further prevented sintering.

Spherulitic crystallization of fluorapatite was observed in glass-ceramics B, C and D after heat treatment at 800° C. According to Granasy: "spatial heterogeneities due to phase separation can provide a source of static disorder giving rise to spherulitic growth" [47]. As mentioned earlier, glass-in-glass phase separation occurs in our compositional range. Moreover, this type of apatite growth was first reported by Carpenter et al., in phase-separated calcium alumino-silicate glasses nucleated with $P_2O_5$ [48], and later described by Shyu and Wu in $MgO$—$CaO$—$SiO_2$—$P_2O_5$ glasses [49]. More recently, Stanton and Hill reported spherulitic heterogeneous nucleation in apatite-mullite glass-ceramics, with an interesting mechanism: phase separation first occurred into amorphous droplets rich in Ca, P and F, surrounded by regions rich in Si and Al [50]. The ensuing crystallization of fluorapatite left the surrounding glass depleted in Ca, P and F, and close to the composition of mullite. As mullite crystallized, the surrounding glass in turn became enriched in Ca. P and F and fluorapatite formed again. A similar route could be happening in composition D, with fluorapatite spherulites crystallizing first, followed by akermanite. This could explain the interpenetrating microstructure obtained after heat treatment at 850° C., temperature at which both phases co-exist. As shown on FIG. 4, it is also possible that the phase-separated area grew larger as the calcium to aluminum ratio increased from composition A to D, leading to progressively larger spherulites.

Compositions C and D are excellent candidates for the production of bioactive ceramic scaffolds by sintering at temperatures as low as 775° C. The unique microstructure conveyed by spherulitic crystallization of fluorapatite may provide an excellent basis for epitaxial growth of apatite crystals. Further crystallization of akermanite could impart additional attractive properties such as enhanced stimulation of cell differentiation into osteoblastic lineage, as suggested by recent studies on sintered akermanite ceramics [51-54].

Increasing the calcium to aluminum ratio led to both a decrease in softening temperature and an increase in crystallization temperature and activation energy for fluorapatite in this compositional range. This led to a widening of the processing window and made possible sintering to near theoretical density at temperatures between 775 and 800° C. for compositions C and D, corresponding to the highest amounts of calcium.

Fluorapatite crystallized following a spherulitic pattern, with increasingly larger spherulites as the calcium to aluminum ratio increased. This microstructure may provide excellent conditions for epitaxial apatite deposition in vivo, as it mimics carbonated apatite crystal habits. The crystallization of akermanite could lead to enhanced stimulation of cell differentiation.

Example 2

(A) Materials and Methods

Four fluorapatite glass compositions in the $SiO_2$—$Al_2O_3$—$P_2O_5$—$MgO$—$Na_2O$—$K_2O$—$CaO$—$CaF_2$ system, with increasing amounts of strontium oxide (D:0, E:12, F:18 and G:24 mol. %) in replacement for calcium oxide (D:23.9 (Table 1), E:12, F:18, G:0 (mol. %) (Table 5), were prepared by twice melting mixtures D-F at 1525° C. for 3 h (Table 5).

TABLE 5

Chemical Composition of Glasses (mol-%)

| | E | F | G |
|---|---|---|---|
| $SiO_2$ | 31.5 | 31.5 | 31.5 |
| MgO | 21.2 | 21.2 | 21.2 |
| $Nb_2O_5$ | 0.2 | 0.2 | 0.2 |
| CaO | 11.9 | 6.0 | 0.0 |
| SrO | 11.9 | 17.9 | 23.9 |
| $Na_2O$ | 2.3 | 2.3 | 2.3 |
| $K_2O$ | 3.8 | 3.8 | 3.8 |
| $Al_2O_3$ | 0.9 | 0.9 | 0.9 |
| $CaF_2$ | 11.2 | 11.2 | 11.2 |
| $P_2O_5$ | 5.0 | 5.0 | 5.0 |
| | 100 | 100 | 100 |

After the second melt, glasses were cast into cylindrical ingots. Differential thermal analyses were performed on powdered glasses to determine glass transition and crystallization temperature.

Disc-shaped specimens (1.2 mm thick, 10 mm in diameter) were sectioned from the ingots. Specimens were heat treated at various temperatures ranging from 775 to 900° C. for 1 h, and analyzed by x-ray powder diffraction (Rigaku Smart-Lab). The density of the glass-ceramics was measured by Archimedes' method.

The chemical solubility was determined on powders after incubation for 120 h at 37° C. in either TRIS-HCl buffer at pH 7.4 or citric acid buffer at pH 3.0, to create either moderate or extreme aging conditions, according to ISO standard 10993-14. The pH of the buffer solutions was measured before and after incubation. Specimens were dried at 80° C. until no further weight loss was observed. The percent weight loss was then calculated for each composition and each buffer. A variable pressure SEM (VP-SEM, Hitachi 3400) coupled with a back-scattered electron detector, was used to perform semi-quantitative EDS analyses of the powders before and after incubation (Bruker AXS microanalyzer).

(B) Results

XRD analyses revealed the formation of both strontium-substituted fluorapatite and strontium-substituted akermanite in the strontium-containing glasses. Differential thermal analyses of powdered glasses showed that the crystallization temperature of Sr-substituted fluorapatite varied only slightly among the compositions. Meanwhile the crystallization temperature for Sr-substituted akermanite increased linearly with strontium content.

The density of the glass-ceramics after heat treatment at 775° C./1 h increased linearly ($R^2$=0.985) with Sr content from 2.951±0.005 for composition D to 3.353±0.021 for composition G. The pH after incubation in TRIS-HCl buffer increased slightly for all compositions. The pH after incubation in citric acid buffer (pH 3) increased markedly for composition G (7.11±0.42) and was highest for composition D (8.58±0.42). The chemical solubility increased as the amount of strontium in the composition increased, reaching a maximum of 2.6±1.2 wt. % in TRIS-HCl buffer and 10.4±0.6 wt. % in citric acid buffer, both for composition G (FIG. 1). The weight loss in citric acid buffer for composition D (4.2±1.2) was not significantly different from that of a synthetic fluorapatite control (4.6±0.6; Clarkson Chromatography, Inc.).

EDS analyses after incubation in citric acid buffer revealed that the Sr-free composition (D) underwent losses in fluorine, sodium and magnesium. Composition E exhibited losses (0.2 to 1.4 at. %) in fluorine, sodium, calcium, strontium, magnesium and potassium. Composition F showed losses (0.3 to 1.8 at. %) in all above species except fluorine. Moderate losses in fluorine and sodium (0.1 to 0.2 at. %) were recorded for Composition G. All compositions, with the exception of D, exhibited very large variations in the amount of silicon after incubation.

(C) Conclusions

Strontium additions in this system led to crystallization of Sr-substituted fluorapatite and Sr-akermanite ((Ca,Sr)$_2$MgSi$_2$O$_7$) The chemical solubility increased with the amount of strontium in the composition in both TRIS-HCl buffer and citric acid buffer. Various species were released during incubation including strontium and calcium. The large variations in silicon content for E, F and G could indicate that the glass network was at various stages of dissolution.

The following references are incorporated by reference herein, as though fully set forth:

[1] Clifford A, Hill R. Apatite-mullite glass-ceramics. Journal of Non-Crystalline Solids, 1996; 196: 346-351.

[2] Kitsugi T, Yamamuro T, Kokubo T. Bonding behavior of a glass-ceramic containing apatite and wollastonite in segmental replacement of the rabbit tibia under load-bearing conditions. Journal of Bone and Joint Surgery-American Volume, 1989; 71A: 264-272.

[3] Kitsugi T, Yamamuro T, Nakamura T, Higashi S, Kakutani Y, Hyakuna K, Ito S, Kokubo T, Takagi M, Shibuya T. Bone bonding behavior of 3 kinds of apatite-containing glass-ceramics. Journal of Biomedical Materials Research, 1986; 20: 1295-1307.

[4] Kokubo T, Ito S, Shigematsu M, Sakka S, Yamamuro T. Mechanical properties of a new type of apatite-containing glass-ceramic for prosthetic application. Journal of Materials Science, 1985; 20: 2001-2004.

[5] Kokubo T, Ito S, Shigematsu M, Sakka S, Yamamuro T. Fatigue and lifetime of bioactive glass-ceramic A-W containing apatite and wollastonite Journal of Materials Science, 1987; 22: 4067-4070.

[6] Juhasz J A, Best S M. Bioactive ceramics: processing, structures and properties. Journal of Materials Science, 2012; 47: 610-624.

[7] Daculsi G, Passuti N, Martin S, Deudon C, Legeros R Z, Raher S. Macroporous Calcium-Phosphate Ceramic for Long-bone Surgery in Humans and Dogs—Clinical and Histological Study Journal of Biomedical Materials Research, 1990; 24: 379-396.

[8] Hench L. Bioactive glasses and glass-ceramics. In: Shackelford J, ed. Bioceramics. Baudrain: Trans Tech Publications, 1999: 37-64.

[9] Hench L, Splinter R, Allen W, Greenlee T. Bonding mechanisms at the interface of ceramic prosthetic materials. Journal of Biomedical Materials Research, 1971; 5: 117-141.

[10] Daculsi G, Legeros R Z, Heughebaert M, Barbieux I. Formation of Carbonate-Apatite Crystals after Implantation of Calcium-Phosphate Ceramics. Calcified Tissue International, 1990; 46: 20-27.

[11] Freeman C O, Brook I M, Johnson A, Hatton P V, Stanton K. Crystallization modifies osteoconductivity in an apatite-mullite glass-ceramic. J Mater Sci-Mater Med, 2003; 14: 985-990.

[12] Davies J E. Bone bonding at natural and biomaterial surfaces. Biomaterials, 2007; 28: 5058-5067.

[13] Dalby M J, Yarwood S J, Riehle M O, Johnstone H J H, Affrossman S, Curtis A S G. Increasing Fibroblast Response to Materials Using Nanotopography: Morphological and Genetic Measurements of Cell Response to 13-nm-High Polymer Demixed Islands. Experimental Cell Research, 2002; 276: 1-9.

[14] Dalby M J, Gadegaard N, Tare R, Andar A, Riehle M O, Herzyk P, Wilkinson C D W, Oreffo R O C. The control of human mesenchymal cell differentiation using nanoscale symmetry and disorder. Nat Mater, 2007; 6: 997-1003.

[15] Denry I L, Holloway J A, Nakkula R J, Walters J D. Effect of niobium content on the microstructure and thermal properties of fluorapatite glass-ceramics. Journal of Biomedical Materials Research Part B-Applied Biomaterials, 2005; 75B: 18-24.

[16] Denry I, Holloway J A, Gupta P K. Effect of crystallization heat treatment on the microstructure of niobium-doped fluorapatite glass-ceramics. Journal of Biomedical Materials Research Part B-Applied Biomaterials, 2012; 100B: 1198-1205.

[17] Kushwaha M, Pan X L, Holloway J A, Denry I L. Differentiation of human mesenchymal stem cells on niobium-doped fluorapatite glass-ceramics. Dental Materials, 2012; 28: 252-260.

[18] O'Flynn K P, Stanton K T. Nucleation and Early Stage Crystallization of Fluorapatite in Apatite-Mullite Glass-Ceramics. Cryst Growth Des, 2010; 10: 1111-1117.

[19] O'Flynn K P, Stanton K T. Controlling the Crystallization of Fluorapatite in Apatite-Mullite Glass-Ceramics. Cryst Growth Des, 2012; 12: 1218-1226.

[20] O'Flynn K P, Twomey B, Breen A, Dowling D P, Stanton K T. Microwave-assisted rapid discharge sintering of a bioactive glass-ceramic. J Mater Sci-Mater Med, 2011; 22: 1625-1631.

[21] Scheffler M, Colombo P. Cellular Ceramics: Structure, Manufacturing, Properties and Applications Weinheim: Wiley-VCH, 2005.

[22] Schwartzwalder K, Somers A V, Inventors; General Motors Corporation, assignee. Method of making porous ceramic articles. U.S. Pat. No. 3,090,094. May 21, 1963.

[23] Rezwan K, Chen Q Z, Blaker J J, Boccaccini A R. Biodegradable and bioactive porous polymer/inorganic composite scaffolds for bone tissue engineering. Biomaterials, 2006; 27: 3413-3431.

[24] Gross K, Bhadang K. Sintered hydroxyfluorapatites. Part III: Sintering and resultant mechanical properties of sintered blends of hydroxyapatite and fluorapatite. Biomaterials, 2004; 25: 1395-1405.

[25] Kothapalli C, Wei M, Vasiliev A, Shaw M T. Influence of temperature and concentration on the sintering behavior and mechanical properties of hydroxyapatite. Acta Mater, 2004; 52: 5655-5663.

[26] Bianco A, Cacciotti I, Lombardi M, Montanaro L, Bemporad E, Sebastiani M. F-substituted hydroxyapatite nanopowders: Thermal stability, sintering behaviour and mechanical properties. Ceramics International, 2010; 36: 313-322.

[27] Tonsuaadu K, Gross K A, Pluduma L, Veiderma M. A review on the thermal stability of calcium apatites. J Therm Anal, 2012; 110: 647-659.

[28] Brauer D S, Anjum M N, Mneimne M, Wilson R M, Doweidar H, Hill R G. Fluoride-containing bioactive glass-ceramics. Journal of Non-Crystalline Solids, 2012; 358: 1438-1442.

[29] Bogdanov B I, Pashev P S, Hristov J H, Markovska I G. Bioactive fluorapatite-containing glass ceramics. Ceramics International, 2009; 35: 1651-1655.

[30] Kansal I, Goel A, Tulyaganov D U, Rajagopal R R, Ferreira J M F. Structural and thermal characterization of $CaO-MgO-SiO_2-P_2O_5-CaF_2$ glasses. Journal of the European Ceramic Society, 2012; 32: 2739-2746.

[31] Kansal I, Tulyaganov D U, Goel A, Pascual M J, Ferreira J M F. Structural analysis and thermal behavior of diopside-fluorapatite-wollastonite-based glasses and glass-ceramics. Acta Biomaterialia, 2010; 6: 4380-4388.

[32] Gutzow I, Pascova R, Karamanov A, Schmelzer J. The kinetics of surface induced sinter crystallization and the formation of glass-ceramic materials. Journal of Materials Science, 1998; 33: 5265-5273.

[33] Lara C, Pascual M J, Duran A. Glass-forming ability, sinterability and thermal properties in the systems $RO-BaO-SiO_2$ (R=Mg, Zn). Journal of Non-Crystalline Solids, 2004; 348: 149-155.

[34] Brink M, Turunen T, Happonen R P, YliUrpo A. Compositional dependence of bioactivity of glasses in the system $Na_2O-K_2O-MgO-CaO-\alpha_2O_3-P_2O_5-SiO_2$. Journal of Biomedical Materials Research, 1997; 37: 114-121.

[35] Bellucci D, Cannillo V, Sola A. Calcium and potassium addition to facilitate the sintering of bioactive glasses. Materials Letters, 2011; 65: 1825-1827.

[36] Duee C, Desanglois F, Lebecq I, Follet-Houttemane C. Predicting glass transition and crystallization temperatures of silicate bioglasses using mixture designs. Journal of Non-Crystalline Solids, 2012; 358: 1083-1090.

[37] Höland W, Beall G. Glass-ceramic technology. 1st edn. Westerville, Ohio: The American Ceramic Society, 2002.

[38] Uhlmann D, Kreidl N. Glass: Science and Technology Orlando, Fla.: Academic Press, Inc., 1983: 465.

[39] Costantini A, Varlese F A, Buri A, Branda F. Effects on the thermal properties and bioactivity of substitution of CaO by $M_2O_3$ (M=La, Y, Al) in wollastonite glass. J Therm Anal, 1998; 52: 975-983.

[40] Hill R G, Brauer D S. Predicting the bioactivity of glasses using the network connectivity or split network models. Journal of Non-Crystalline Solids, 2011; 357: 3884-3887.

[41] Marotta A, Buri A, Branda F. Nucleation in glass and differential thermal analysis. Journal of Materials Science, 1981; 16: 341-344.

[42] Kissinger H. Reaction Kinetics in Differential Thermal Analysis. Anal Chem, 1957; 29: 1702-1706.

[43] Hill R G, O'Donnell M D, Law R V, Karpukhina N, Cochrane B, Tulyaganov D U. The early stages of nucleation and crystallisation of an apatite glass-ceramic: Evidence for nano-scale crystallisation. Journal of Non-Crystalline Solids, 2010; 356: 2935-2941.

[44] Shyu J J, Wu J M. Effects of composition changes on the crystallization behavior of $MgO-CaO-SiO_2-P_2O_5$ glass-ceramics Journal of the American Ceramic Society, 1991; 74: 2123-2130.

[45] Stanton K, Hill R. The role of fluorine in the devitrification of $SiO_2-Al_2O_3-P_2O_5-CaO-CaF_2$ glasses. Journal of Materials Science, 2000; 35: 1911-1916.

[46] Rafferty A, Clifford A, Hill R, Wood D, Samuneva B, Dimitrova-Lukacs M. Influence of fluorine content in apatite-mullite glass-ceramics. Journal of the American Ceramic Society, 2000; 83: 2833-2838.
[47] Granasy L, Pusztai T, Tegze G, Warren J A, Douglas J F. Growth and form of spherulites. Phys Rev E, 2005; 72.
[48] Carpenter P R, Campbell M, Rawlings R D, Rogers P S. Spherulitic growth of apatite in a glass-ceramic system Journal of Materials Science Letters, 1986; 5: 1309-1312.
[49] Shyu J J, Wu J M. Spherulitic growth of apatite in a MgO—CaO—SiO$_2$—P$_2$O$_5$ glass Journal of the American Ceramic Society, 1991; 74: 1532-1540.
[50] Stanton K T, Hill R G. Crystallisation in apatite-mullite glass-ceramics as a function of fluorine content. Journal of Crystal Growth, 2005; 275: E2061-E2068.
[51] Huang Y, Jin X G, Zhang X L, Sun H L, Tu J W, Tang T T, Chang J, Dai K R. In vitro and in vivo evaluation of akermanite bioceramics for bone regeneration. Biomaterials, 2009; 30: 5041-5048.
[52] Hou X N, Yin G F, Chen X C, Liao X M, Yao Y D, Huang Z B. Effect of akermanite morphology on precipitation of bone-like apatite. Applied Surface Science, 2011; 257: 3417-3422.
[53] Gu H J, Guo F F, Zhou X, Gong L L, Zhang Y, Zhai W Y, Chen L, Cen L, Yin S, Chang J, Cui L. The stimulation of osteogenic differentiation of human adipose-derived stem cells by ionic products from akermanite dissolution via activation of the ERK pathway. Biomaterials, 2011; 32: 7023-7033.
[54] Xia L G, Zhang Z Y, Chen L, Zhang W J, Zeng D L, Zhang X L, Chang J, Jiang X Q. Proliferation and osteogenic differentiation of human periodontal ligament cells on akermanite and beta-TCP bioceramics European Cells & Materials, 2011; 22: 68-83.

What is claimed:

1. A fluorapatite glass-ceramic body prepared by a process comprising:
   (a) providing powdered glass by heating a SiO$_2$—Al$_2$O$_3$—P$_2$O$_5$—MgO—Na$_2$O—K$_2$O—CaO—CaF$_2$ mixture having a CaO:Al$_2$O$_3$ mole-ratio of about 2.5-30:1;
   (b) compacting the powdered glass into a solid form; and
   (c) heating the solid form to about 650-1050° C. for a time sufficient to yield a sintered fluorapatite glass-ceramic body.

2. A fluorapatite glass-ceramic body prepared by a process comprising:
   (a) producing powdered glass by heating a mixture of SiO$_2$—Al$_2$O$_3$—P$_2$O$_5$—MgO—Na$_2$O—K$_2$O—CaF$_2$, comprising SrO or a combination of CaO and SrO having a mole ratio of SrO to Al$_2$O$_3$ of about 2.5-30:1;
   (b) compacting the powdered glass into a solid firm; and
   (c) heating the solid form to about 650° C.-1050° C. for a time sufficient to yield a sintered fluorapatite glass-ceramic body.

3. The body of claim 1 wherein SrO is absent.

4. The body of claim 2 wherein both SrO and CaO are present.

5. The body of claim 2 wherein CaO is absent and SrO is present.

6. The body of claim 1 or 2 wherein step (c) is carried out at about 700° C.-900° C.

7. The body of claim 1 or 2 wherein the degree of sintering in step (c) is about 90-99.5%.

8. The body of claim 1 wherein the CaO:Al$_2$O$_3$ mole-ratio is about 3-25:1.

9. The body of claim 2 wherein the SrO:CaO mole ratio is about 3-1:1.

10. The body of claim 3 wherein the solid form is sintered at about 750-800° C.

11. The body of claim 10 wherein the heating is carried out for about 0.25-5.0 hrs.

12. The body of claim 1 or 2 wherein the glass comprises niobium.

13. The body of claim 1 that comprises flower-shaped fluorapatite crystals substantially as shown in FIG. 4, Panels C or D.

14. The body of claim 1 wherein the fluorapatite glass of step (a) is prepared by melting a mixture of the composition:

| Ingredient | wt-% |
|---|---|
| SiO$_2$ | 28-38 |
| MgO | 12-18 |
| Nb$_2$O$_5$ | 1-5 |
| CaO | 20-30 |
| Na$_2$O | 1-3 |
| K$_2$O | 5-8 |
| Al$_2$O$_3$ | 0.5-7.5 |
| CaF$_2$ | 4-6 |
| P$_2$O$_5$ | 10-14. |

15. The body of claim 14 further comprising SrO.

16. The body of claim 1 wherein the fluorapatite glass of step (a) is prepared by melting a composition of the formulas C-D:

| | Composition (mole-%) | |
|---|---|---|
| | C | D |
| SiO$_2$ | 32.3 | 31.5 |
| MgO | 21.8 | 21.2 |
| Nb$_2$O$_5$ | 0.2 | 0.2 |
| CaO | 19.0 | 23.9 |
| Na$_2$O | 2.4 | 2.3 |
| K$_2$O | 3.9 | 3.8 |
| Al$_2$O$_3$ | 3.9 | 0.9 |
| CaF$_2$ | 11.5 | 11.2 |
| P$_2$O$_5$ | 5.1 | 5.0. |

17. The body of claim 16 wherein the solid form prepared from composition C is heated at about 700° C.-900° C. or the solid form prepared from composition D is heated at about 775° C.-950° C.

18. The body of claim 2 wherein the fluorapatite glass of step (a) is prepared by melting a composition of the formulas E-G:

| | Composition (mole-%) | | |
|---|---|---|---|
| | E | F | G |
| SiO$_2$ | 31.5 | 31.5 | 31.5 |
| MgO | 21.2 | 21.2 | 21.2 |
| Nb$_2$O$_5$ | 0.2 | 0.2 | 0.2 |
| CaO | 11.9 | 6.0 | 0.0 |
| SrO | 11.9 | 17.9 | 23.9 |
| Na$_2$O | 2.3 | 2.3 | 2.3 |
| K$_2$O | 3.8 | 3.8 | 3.8 |
| Al$_2$O$_3$ | 0.9 | 0.9 | 0.9 |
| CaF$_2$ | 11.2 | 11.2 | 11.2 |
| P$_2$O$_5$ | 5.0 | 5.0 | 5.0. |
| | 100 | 100 | 100 |

19. The body of claim 1 or 2 further comprising stem cells cultured thereupon.

20. The body of claim 19 wherein the stem cells are hMSCs.

21. A therapeutic method comprising implanting a shaped body of claim 1 or 2 in vivo in an amount effective to stimulate bone growth in a mammal.

22. The method of claim 21 wherein the mammal is a human.

23. The glass of step (a) of claim 1 or 2.

24. A bone filler, bone replacement material or bone graft material formed from the fluorapatite glass-ceramic body of claim 1 or 2.

25. A glass-ceramic scaffold formed from the fluorapatite glass-ceramic body of claim 1 or 2.

* * * * *